United States Patent
Lan et al.

(10) Patent No.: US 12,121,690 B2
(45) Date of Patent: Oct. 22, 2024

(54) METHODS AND DEVICE FOR PERFORMING CARDIOLOGY AND ENDOVASCULAR INTERVENTIONAL OPERATIONS VIA RADIAL ARTERY OR ULNAR ARTERY

(71) Applicant: Ming Lan, Beijing (CN)

(72) Inventors: Ming Lan, Beijing (CN); Yu Meng, Beijing (CN)

(73) Assignees: Ming Lan, Beijing (CN); Yu Meng, Beijing (CN)

( * ) Notice: Subject to any disclaimer, the term of this patent is extended or adjusted under 35 U.S.C. 154(b) by 825 days.

(21) Appl. No.: 17/278,176

(22) PCT Filed: Dec. 30, 2019

(86) PCT No.: PCT/CN2019/129865
§ 371 (c)(1),
(2) Date: Mar. 19, 2021

(87) PCT Pub. No.: WO2021/036143
PCT Pub. Date: Mar. 4, 2021

(65) Prior Publication Data
US 2021/0346667 A1 Nov. 11, 2021

(30) Foreign Application Priority Data
Aug. 29, 2019 (CN) .......................... 201921422605.4

(51) Int. Cl.
*A61M 39/02* (2006.01)
*A61B 10/04* (2006.01)
(Continued)

(52) U.S. Cl.
CPC ......... *A61M 39/0247* (2013.01); *A61B 10/04* (2013.01); *A61B 10/06* (2013.01);
(Continued)

(58) Field of Classification Search
CPC ......... A61B 10/04; A61B 10/06; A61B 17/12; A61B 17/29; A61B 17/34;
(Continued)

(56) References Cited

U.S. PATENT DOCUMENTS

2002/0177772 A1* 11/2002 Altman ................... B82Y 5/00
600/431
2008/0015546 A1* 1/2008 Casas ................. A61K 49/0461
604/93.01
(Continued)

FOREIGN PATENT DOCUMENTS

| CN | 102362808 A | 2/2012 |
| CN | 110037754 A | 7/2019 |

OTHER PUBLICATIONS

Choudhury et al. "Transradial approach for left ventricular endomyocardial biopsy." Canadian Journal of Cardiology 34.10 (2018): 1283-1288. (Year: 2018).*
(Continued)

*Primary Examiner* — Amelie R Davis
(74) *Attorney, Agent, or Firm* — AKC PATENTS, LLC; Aliki K. Collins (57) ABSTRACT

A method for performing cardiology and endovascular interventional operations includes: Step 1, putting an artery sheath into a punctured artery; inserting a Pigtail catheter into a first end of the artery sheath, and advancing it to a left ventricle; injecting contrast into the Pigtail catheter to perform left ventricle angiography; and withdrawing the Pigtail catheter from the artery sheath. Step 2, inserting a guiding catheter into the first end of the artery sheath, and advancing it to the left ventricle. Step 3, advancing a myocardial biopsy forcep to a left ventricle endocardium through the guiding catheter to collect a piece of myocardium. Step 4, withdrawing the myocardial biopsy forcep from the guiding catheter, and preserving a myocardium specimen. Step 5, repeating
(Continued)

steps 3 and 4 until collecting enough number of myocardium specimens. Step 6, withdrawing the guiding catheter from the artery sheath, and pulling the artery sheath out of the artery.

17 Claims, 3 Drawing Sheets

(51) Int. Cl.
  *A61B 10/06* (2006.01)
  *A61B 17/00* (2006.01)
  *A61M 5/00* (2006.01)
  *A61M 25/00* (2006.01)

(52) U.S. Cl.
  CPC ... *A61M 5/007* (2013.01); *A61B 2017/00243* (2013.01); *A61M 25/0068* (2013.01); *A61M 2039/0258* (2013.01); *A61M 2039/0279* (2013.01)

(58) Field of Classification Search
  CPC ............ A61B 2017/00243; A61B 5/00; A61B 5/0215; A61M 2039/0258; A61M 2039/0279; A61M 25/0068; A61M 39/0247; A61M 5/007
  See application file for complete search history.

(56) References Cited

U.S. PATENT DOCUMENTS

| 2008/0017691 A1* | 1/2008 | Hausen ............... A61B 17/0644 227/175.1 |
| 2012/0059248 A1 | 3/2012 | Holsing et al. |
| 2015/0005813 A1 | 1/2015 | Maslanka et al. |
| 2015/0112210 A1* | 4/2015 | Webler ................. A61B 5/6851 600/486 |

OTHER PUBLICATIONS

Kai et al. "A 6-Fr guiding catheter (Slim Guide(®)) for use with multiple microdevices." Surg Neurol Int. 2012;3:59. (Year: 2012).*
Glidesheath Slender Pocket Guide. Terumo Intl. Systems, 2018. (Year: 2018).*
Schulz et al. "Feasibility and safety of left ventricular endomyocardial biopsy via transradial access: Technique and initial experience." Catheter Cardiovasc Interv. Oct. 2015; 86(4):761-5. (Year: 2015).*
Schussler. "Effectiveness and safety of transradial artery access for cardiac catheterization." Proc (Bayl Univ Med Cent). Jul. 2011; 24(3):205-9. (Year: 2011).*
ISR for PCT/CN2019/129865, Dec. 30, 2019.
Lan, Ming et al.; Initial application of transradial left ventricular endomyocardial biopsy in diagnosis of cardiomyopathy, Chinese Journal of Cardiovascular Medicine, vol. 23, No. 3, (Jun. 25, 2018).

* cited by examiner

METHODS AND DEVICE FOR PERFORMING CARDIOLOGY AND ENDOVASCULAR INTERVENTIONAL OPERATIONS VIA RADIAL ARTERY OR ULNAR ARTERY

TECHNICAL FIELD

The present invention relates to the technical field of cardiology and endovascular interventional operations, in particular to methods and a device for performing cardiology and endovascular interventional operations such as an endomyocardial biopsy via a radial artery or ulnar artery.

BACKGROUND

An endomyocardial biopsy is a sampling technology for a cardiac examination and is a representative cardiac interventional operation. Pathology results of the endomyocardial biopsy serve as gold standards for diagnosis of non-ischemic cardiomyopathy and have important clinical significance in diagnosis of myocarditis, etiological diagnosis of unexplained heart failure, monitoring of heart transplantation postoperative rejections, etc.

The endomyocardial biopsy includes a left ventricle endomyocardial biopsies (hereinafter referred to as 'LV-EMB' that should be completed via an artery) and a right ventricle endomyocardial biopsy (hereinafter referred to as 'RV-EMB' that should be completed via a vein). The RV-EMB inserts a catheter into a vein such as a jugular vein, a subclavian vein and a femoral vein and puts in myocardial biopsy forceps through venous catheterization to clamp a myocardium mostly in an interventricular septum. However, a right ventricle has a thin wall (generally less than 4 mm in thickness), leading to complications such as cardiac perforation during the myocardial biopsy, and a left ventricle usually has a thicker wall (about 10 mm in thickness), so the RV-EMB has lower safety compared to the LV-EMB. Then, the RV-EMB can only conduct sampling in an interventricular septum under most circumstances within a limited sampling range. However, the clinical consequences of many relevant pathologies affect predominantly the left ventricle, for example, in most cases of cardiomyopathy or myocarditis. Thus the RV-EMB has lower effectiveness compared to the LV-EMB. Yilmaz et al (Yilmaz A, Kindermann I, Kindermann M, Mahfoud F, Ukena C, Athanasiadis A, Hill S, Mahrholdt H, Voehringer M, Schieber M, Klingel K, Kandolf R, Böhm M, Sechtem U. Comparative evaluation of left and right ventricular endomyocardial biopsy: differences in complication rate and diagnostic performance. Circulation. 2010; 122:900-909. doi: 10.1161/CIRCULATION-AHA.109.924167.) demonstrated a higher yield for detection of myocarditis in LV or biventricular EMB than in RV biopsies alone. The same finding was noted in a recent retrospective series of 136 patients in which the sensitivity of LV biopsies was 3-fold higher than that of RV biopsies. Chimenti and Frustaci (Chimenti C, Frustaci A. Contribution and risks of left ventricular endomyocardial biopsy in patients with cardiomyopathies: a retrospective study over a 28-year period. Circulation. 2013; 128:1531-1541. doi: 10.1161/CIRCULATIONAHA.13.001414.) reported that in patients subjected to biventricular EMB, LV samples revealed diagnostic clues in 96.3% of cases (2307 patients) versus 71.4% (1711 patients) in RV tissue (P<0.001). Especially when the structural and functional abnormalities affected exclusively the LV, the diagnostic yield of LVEMB was 97.8% compared with 53% for RVEMB. In the context of myocarditis, the most frequent finding was lymphocytic infiltration (95.5%), followed by eosinophilic infiltrates (3.6%) or giant cells/sarcoidosis granulomas (together 0.9%). Of note, in this study, LV biopsy also had a better safety profile than RV biopsy, although LV-EMB were taken mainly from the seemingly more risk-prone free wall and RV-EMB from the septum. In addition, some myocardial biopsy patients need to be treated with cardiology and endovascular interventional operations, such as coronary angiography and/or intervention, left ventricle angiography and others which may be completed via an artery, if they adopt the RV-EMB, sheaths and catheters need to be inserted into both an artery and a vein, as a result, operations are relatively complicated, complication risk may be increased, and patients may have to undergo greater pains. Thus, compared to the RV-EMB, the LV-EMB is safer, more effective and more convenient.

At present, one type of LV-EMB is executed via a femoral artery. Since the femoral artery has a large diameter (about 8 mm), there are high risks of bleeding and puncture site complications (such as vasovagal reflex, arterio-venous fistula and retroperitoneal hematoma). Another type of LV-EMB is executed via a radial artery and adopts a Sheathless guiding catheter technology, specifically including the operation steps: 1, puncturing a radial artery to insert an artery sheath, and putting in an apparatus through the artery sheath to complete corresponding operations (decided according to specific clinical conditions); 2, withdrawing the apparatus from the artery sheath; 3, withdrawing the artery sheath, remaining a guide wire in the artery, and at the moment, pressing a puncture site of the radial artery by a surgical doctor to avoid bleeding; 4, putting a Sheathless guiding catheter with an dilator into the radial artery through the guide wire by the operator with the help of an assistant to be advanced to an ascending aorta via an brachial artery and a subclavian artery; 5, withdrawing the dilator from the Sheathless guiding catheter, and advancing a Pigtail catheter into the Sheathless guiding catheter to enable the Sheathless guiding catheter and the Pigtail catheter to enter a left ventricle at the same time; and 6, withdrawing the Pigtail catheter, remaining the Sheathless guiding catheter in the left ventricle, and collect myocardia from an interventricular septum or free walls through myocardial biopsy forcep advanced via the Sheathless guiding catheter. In the process above, when the Sheathless guiding catheter that is about 100 cm in length is allowed to penetrate into the radial artery continuously and is rotated, pushed and pulled during the procedure, the puncture site of the radial artery may be directly and continuously stimulated, which may easily cause the radial artery spasm. Severe radial artery spasm may cause operation failure, and there have been cases that operation failures of the Sheathless guiding catheter so far. In addition, after the artery sheath is withdrawn from the radial artery, the puncture site needs to be pressed continuously, so too much bleeding may be easily caused by improper coordination of operators and assistants; and the Sheathless guiding catheter has a soft head and usually cannot cooperate with its dilator well, so complications such as injuries of great vessels may be easily caused during the procedure through the great vessels.

SUMMARY

For the problems existing in the prior art, the present invention aims to provide methods and a device for performing cardiology and endovascular interventional operations such as an endomyocardial biopsy via a radial artery or ulnar artery. The methods only need to insert one sheath into a radial artery or ulnar artery once during cardiology and/or endovascular interventional operations including LV-EMB, thereby preventing catheter inserting into blood vessels at multiple sites and reducing probability of traumas and other complications. The patients need not to lie on the beds, and immediate patient mobilization can be achieved after operations. The patients feel more comfortable and have lower risk of complications of lying on the beds, such as deep vein thrombosis and hypostatic pneumonia, among others. Compared to an existing Sheathless guiding catheter technology via a radial artery, the methods can increase the success rate of operations by reducing repeated stimuli to a puncture site, increasesafety of operations by reducing bleeding and great vessels injuries' risk, and increase the effectiveness of operations, as an interventional "one stop shop" technique. In addition, the methods are easy to grad with short learning curve, and conducive to the future application.

In order to achieve the aforementioned aim, the technical solution of the present invention is described as follows:

A method for performing cardiology and endovascular interventional operations via a radial artery or ulnar artery includes:
step 1, putting an artery sheath into a punctured artery, wherein the artery is a radial artery or ulnar artery;
step 2, allowing a guiding catheter to penetrate into the artery sheath from outside the body and penetrate out of the artery sheath from the other end to be advanced to a left ventricle;
step 3, advancing a myocardial biopsy forcep to a left ventricle endocardium through the guiding catheter to collect a piece of myocardium;
step 4, withdrawing the myocardial biopsy forcep from the guiding catheter to be outside the body, and preserving a myocardium specimen;
step 5, repeating the step 3 and the step 4 until collecting enough number of myocardium specimens; and
step 6, withdrawing the guiding catheter from the artery sheath, pulling the artery sheath out of the artery, and performing compression dressing over the access site.

Further, before pulling the artery sheath out of the artery, the method further includes the following steps:
allowing an angiography catheter to penetrate into the artery sheath from outside the body and penetrate out of the artery sheath from the other end to be advanced to an aortic sinus;
injecting contrast into the angiography catheter for coronary angiography; and
withdrawing the angiography catheter from the artery sheath after completing the coronary angiography.

Further, before pulling the artery sheath out of the artery, the method further includes the following steps:
allowing a Pigtail catheter to penetrate into the artery sheath from outside the body and penetrate out of the artery sheath from the other end to be advanced to the left ventricle;
injecting contrast into the Pigtail catheter for left ventricle angiography; and
withdrawing the Pigtail catheter from the artery sheath after completing the left ventricle angiography.

Further, before the step 1, the method further includes the step of: performing sterilization, draping and local anesthesia on a puncture site of the radial artery or ulnar artery.

Further, before the step 5, the method further includes the step of: injecting contrast into the guiding catheter for left ventricle angiography.

The present invention further provides another method for performing cardiology and endovascular interventional operations via a radial artery or ulnar artery. The method includes:
step 1, allowing a guiding catheter to penetrate into an artery sheath from outside the body and penetrate out of the artery sheath from the other end to be advanced to an aortic sinus;
step 2, injecting contrast through the guiding catheter for coronary angiography, and/or allowing a coronary interventional therapy apparatus to enter through the guiding catheter for a coronary interventional therapy operation;
step 3, advancing the guiding catheter to a left ventricle after completing the coronary angiography and/or the coronary interventional therapy operation;
step 4, advancing a myocardial biopsy forcep to a left ventricle endocardium through the guiding catheter to collect a piece of myocardium;
step 5, withdrawing the myocardial biopsy forcep from the guiding catheter to be outside the body, and preserving a myocardium specimen;
step 6, repeating the step 3 and the step 4 until collecting enough number of myocardium specimens; and
step 7, withdrawing the guiding catheter from the artery sheath, pulling the artery sheath out of the artery, and performing compression dressing over the access site.

Further, before pulling the artery sheath out of the artery, the method further includes the step of: injecting contrast into the guiding catheter for left ventricle angiography.

The present invention further provides another method for performing cardiology and endovascular interventional operations via a radial artery or ulnar artery. The method includes:
step 1, allowing a guiding catheter to penetrate into an artery sheath from outside the body and penetrate out of the artery sheath from the other end to be advanced to an aortic sinus;
step 2, injecting contrast through the guiding catheter for peripheral artery angiography, and/or allowing a peripheral artery interventional therapy apparatus to enter through the guiding catheter for a peripheral artery interventional therapy operation;
step 3, advancing the guiding catheter to a left ventricle after completing the peripheral artery angiography and/or the peripheral artery interventional therapy operation; step 4, advancing a myocardial biopsy forcep to a left ventricle endocardium through the guiding catheter to collect a piece of myocardium;
step 5, withdrawing the myocardial biopsy forcep from the guiding catheter to be outside the body, and preserving a myocardium specimen, repeating the step 3 and the step 4 until collecting enough number of specimens; and step 6, withdrawing the guiding catheter from the artery sheath, pulling the artery sheath out of an artery, and performing compression dressing over the access site.

Further, before pulling the artery sheath out of an artery, the method further includes the step of: injecting contrast into the guiding catheter for left ventricle angiography.

The present invention further provides a device for performing cardiology and endovascular interventional operations via a radial artery or ulnar artery. The device includes an artery sheath, a guiding catheter and a myocardial biopsy forcep, wherein the artery sheath is configured to be put into a punctured artery of the radial artery or ulnar artery, the guiding catheter can penetrate out of the artery sheath into the artery and can be advanced to an aorta, a peripheral artery, an aortic sinus or a left ventricle, and the myocardial biopsy forcep can penetrate out of the guiding catheter to be advanced to the left ventricle and are configured to collect myocardia.

Further, the device further includes a Y-shaped hemostasis valve, wherein the Y-shaped hemostasis valve includes three ports communicating with one another, the first port of the Y-shaped hemostasis valve linearly communicates with the second port of the Y-shaped hemostasis valve, a hemostasis valve body is disposed at the second port of the Y-shaped hemostasis valve, the first port of the Y-shaped hemostasis valve communicates with an in-vitro port of the guiding catheter, and the myocardial biopsy forcep penetrate into the Y-shaped hemostasis valve via the guiding catheter from the second port of the Y-shaped hemostasis valve.

Further, the device includes a three-way stopcock, a pressure transducer, a pressure monitor and contrast injection system, wherein a first port of the three-way stopcock communicates with the third port of the Y-shaped hemostasis valve, a second port of the three-way stopcock is connected with the pressure transducer and the contrast injection system, and the pressure transducer is connected with the pressure monitor.

Further, a rotary switch is disposed at the three-way stopcock and is configured to connect or disconnect any two ports of the three-way stopcock.

Further, the device further includes an angiography catheter, wherein the angiography catheter can penetrate out of the artery sheath into the artery and can be advanced to an aorta, a peripheral artery, an aortic sinus or a left ventricle.

Further, the device further includes a three-way stopcock, a pressure transducer, a pressure monitor and contrast injection system, wherein a first port of the three-way stopcock communicates with an in-vitro port of a angiography catheter, a second port of the three-way stopcock is connected with the pressure transducer and the contrast injection system, and the pressure transducer is connected with the pressure monitor.

Further, the device further includes a Pigtail catheter, wherein the Pigtail catheter can penetrate out of the artery sheath into the artery and can be advanced to an aorta, a peripheral artery, an aortic sinus or a left ventricle.

Further, the device further includes a three-way stopcock, a pressure transducer, a pressure monitor and contrast injection system, wherein a first port of the three-way stopcock communicates with an in-vitro port of the Pigtail catheter, a second port of the three-way stopcock is connected with the pressure transducer and the contrast injection system, and the pressure transducer is connected with the pressure monitor.

Further, the size ranges of a length, an outer diameter and an inner diameter of the artery sheath are 3-40 cm, 1.40-3.53 mm and 1.30-3.40 mm, respectively, the size ranges of a length, an outer diameter and an inner diameter of the guiding catheter are 30-140 cm, 1.30-3.40 mm and 1.20-3.30 mm, respectively, and the size ranges of a length and an outer diameter of the myocardial biopsy forceps are 31-180 cm and 0.10-3.30 mm, respectively.

Further, the difference of the outer diameter of the guiding catheter and the inner diameter of the artery sheath is greater than or equal to 0.003 mm, and the difference of the outer diameter of the myocardial biopsy forceps and the inner diameter of the guiding catheter is greater than or equal to 0.003 mm.

Figure 1:
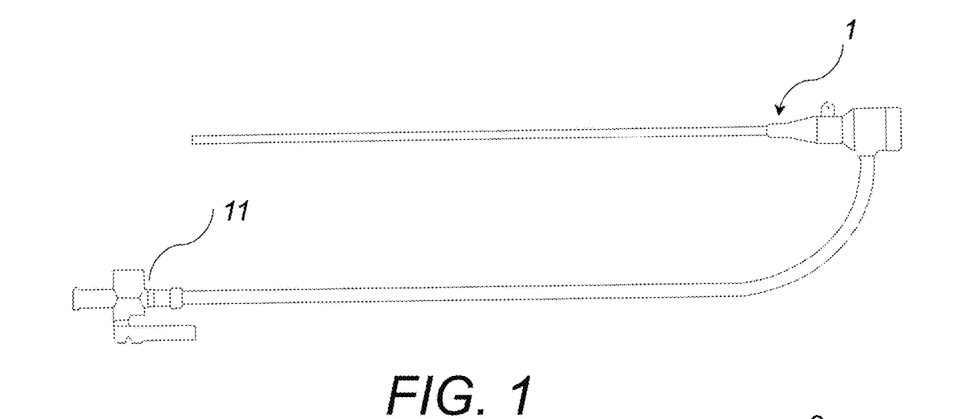
FIG. 1 is a structural schematic diagram of an artery sheath in an embodiment of the present invention.

IN FIGURES 1. artery sheath; 11. hemostasis valve;
2. guiding catheter;
3. myocardial biopsy forcep; 31. forcep body; 32. handle;
4. angiography catheter; 5. Y-shaped hemostasis valve; 6. pressure transducer; 7. pressure monitor; 8. three-way stopcock; 9. contrast injection system; 10. hemostasis valve body; 12. Pigtail catheter.

DETAILED DESCRIPTION

The present invention is described below in combination with the examples to clearly describe the design concept of the present invention.

The technical solution in embodiments of the present invention is clearly and completely described below in combination with the drawings in examples of the present invention to make those skilled in the art better understand the solution of the present invention. Obviously, the described examples are only some examples of the present invention, not all of the examples. All other embodiments obtained by those of ordinary skills in the art without creative labor based on the examples of the present invention shall be within the protection scope of the present invention.

It is important to note that terms used herein are only used for describing specific embodiments, but not intend to limit exemplary embodiments according to the present invention. As used herein, the singular forms intend to include plural forms unless the context clearly dictates otherwise. In addition, it is to be further understood that the terms "comprising" and/or "including" used in the present description indicate the presence of features, steps, operations, devices, assemblies and/or their combinations.

For a clearer description of the technical solution of the present invention, the present invention is described in details by reference to the accompanying drawings in conjunction with the embodiments. The embodiments in the present invention and features in the embodiments can be combined without one another.

Embodiment 1

This embodiment provides a first implementation of a method for performing cardiology and endovascular interventional operations via a radial artery or ulnar artery of the present invention. The method is a method for performing endomyocardial biopsies and includes:

step 1, putting an artery sheath into a punctured artery, wherein the artery is a radial artery or ulnar artery;

wherein before the step 1, conventional sterilization, draping and local anesthesia are firstly performed on a punctured site of the radial artery or ulnar artery of a patient, and then the radial artery or ulnar artery is punctured, wherein whether the radial artery is used or the ulnar artery is used for the operation is determined according to specific conditions of the patient.

step 2, allowing a guiding catheter to penetrate into the artery sheath from outside the body and penetrate out of the artery sheath from the other end through a short guide wire to be advanced to a left ventricle, withdrawing the short guide wire and remaining the guiding catheter in the left ventricle;

step 3, advancing a myocardial biopsy forcep to a left ventricle endocardium through the guiding catheter to collect a piece of myocardium; specifically, adjusting the position of the myocardial biopsy forcep in perspective, withdrawing the myocardial biopsy forcep by about 1.0 cm, opening the forcep, advancing the myocardial biopsy forcep back to the left ventricle endocardium, once feeling resistance, rapidly closing the punch, and stably withdrawing the myocardial biopsy forcep to get away from a left ventricle wall while guaranteeing that the punch is in a closed state; wherein before the step 3, the myocardial biopsy forcep are wiped with a heparin saline gauze, in the above process, the position of the guiding catheter can be adjusted such that the myocardial biopsy forcep can reach different positions to take myocardia, and the guiding catheter does not continuously simulate a puncture site, thereby further reducing the probability of vasospasm and increasing the success rate of operation;

step 4, withdrawing the myocardial biopsy forcep from the guiding catheter to be outside the body, and preserving a myocardium specimen; wherein 4-10 pieces of myocardia can be respectively collected from an interventricular septum and free walls of the left ventricle by executing the step 3 and the step 4 repeatedly, in the interval between two adjacent biopsies, heparin saline is used for flushing the guiding catheter and cleaning the myocardial biopsy forcep, and after there is blood flowing out of the guiding catheter, the heparin saline is used for cleaning the myocardial biopsy forcep and flushing the guiding catheter, thereby preventing thrombus and fallen myocardia probably existing in the guiding catheter from being flushed into the left ventricle to cause peripheral artery embolism;

step 5, repeating the step 3 and the step 4 until collecting enough number of myocardium specimens; and step 6, withdrawing the guiding catheter from the artery sheath through a short guide wire, pulling the artery sheath out of the artery, and performing compression dressing over the access site.

In this embodiment, before the step 5, left ventricle angiography can further be alternately performed, that is, after a myocardial biopsy is completed, contrast is injected into the guiding catheter for the left ventricle angiography, thereby avoiding myocardial perforation and other complications.

By means of the method for performing the endomyocardial biopsy in this embodiment, after the catheter is inserted into the blood vessel of the radial artery or ulnar artery, there is no need to insert catheters into blood vessels of other sites in the operation, and there is no need to withdraw the artery sheath from the blood vessel of the artery to be replaced with other sheath catheters or Sheathless guiding catheters neither, so the patient does not need to lie on a bed after the operation and feels more comfortable, relevant complications caused by stimuli to the puncture site or lying on the bed (such as deep vein thrombus and hypostatic pneumonia) can be reduced, and meanwhile, the probability of arteriospasm caused by replacing the long sheath catheter, the bleeding risk in the exchanging process of the sheath catheter and the probability of hematoma of the puncture site and other complications may be reduced.

Embodiment 2

This embodiment provides a second implementation of a method for performing cardiology and endovascular interventional operations via a radial artery or ulnar artery of the present invention. The method is a method for performing coronary angiography and endomyocardial biopsy in a cardiology interventional operation and includes: step 1, putting an artery sheath into a punctured artery, wherein the artery is a radial artery or a ulnar artery;

wherein before the step 1, conventional sterilization, draping and local anesthesia are firstly performed on a punctured site of the radial artery or ulnar artery of a patient, and then the radial artery or ulnar artery is punctured, wherein whether the radial artery is used or the ulnar artery is used for the operation is determined according to specific conditions of the patient.

step 2, allowing an angiography catheter to penetrate into the artery sheath from outside the body and penetrate out of the artery sheath from the other end through a short guide wire to be advanced to an aortic sinus, and withdrawing the short guide wire, wherein the artery has a small diameter at the puncture site and gradually increases its diameter from the puncture site to the aortic sinus, so the artery sheath does not need to be too long, when the angiography catheter penetrates out of the artery sheath from the other end where the diameter of the artery has already been increased, the angiography catheter may quite easily penetrate into the aortic sinus from the artery at such position, the artery sheath disposed in the artery makes sure that the angiography catheter may stably penetrate into the aortic sinus, and in this way, the puncture site is not continuously stimulated, thereby reducing the probability of vasospasm and increasing the success rate of operation.

step 3, adjusting the angiography catheter to left and right coronary ostia respectively, and injecting contrast into the angiography catheter for coronary angiography;

step 4, after completing the coronary angiography, withdrawing the angiography catheter from the coronary ostia, and allowing the short guide wire to penetrate into the angiography catheter from an in-vitro end and penetrate out of the angiography catheter from the other end located in the artery so as to withdraw the angiography catheter from the artery sheath and remain the short guide wire in the artery, wherein the angiography catheter may not continuously stimulate the puncture site when being withdrawn from the artery sheath;

step 5, allowing a guiding catheter to penetrate into the artery sheath from outside the body and penetrate out of the artery sheath from the other end through a short guide wire to be advanced to a left ventricle with the aid of the short guide wire, withdrawing the short guide wire and remaining the guiding catheter in the left ventricle, wherein the artery has a small diameter at the puncture site and gradually increases its diameter from the puncture site to the left ventricle, so the artery sheath does not need to be too long, when the guiding catheter penetrates out of one end of the artery sheath disposed in the artery where the diameter of the artery has already been increased, the guiding catheter may quite easily penetrate into the left ventricle from the artery at such position, the artery sheath disposed in the artery makes sure that the guiding catheter may stably penetrate into the left ventricle, and in this way, the puncture site cannot be continuously stimulated, thereby reducing the probability of vasospasm and increasing the success rate of operation;

step 6, advancing a myocardial biopsy forcep to a left ventricle endocardium through the guiding catheter to collect a piece of myocardium; specifically, adjusting the position of the myocardial biopsy forcep in perspective, withdrawing the myocardial biopsy forcep by about 1.0 cm, opening a punch, advancing the myocardial biopsy forcep back to the left ventricle endocardium, once feeling resistance, rapidly closing the punch, and stably withdrawing the myocardial biopsy forcep to get away from a left ventricle wall while guaranteeing that the punch is in a closed state; wherein before the step 6, the myocardial biopsy forcep are wiped with a heparin saline gauze, in the above process, the position of the guiding catheter can be adjusted such that the myocardial biopsy forcep can reach different positions to take myocardia, and the guiding catheter is not continuously simulate a puncture site, thereby further reducing the probability of vasospasm and increasing the success rate of operation;

step 7, withdrawing the myocardial biopsy forcep from the guiding catheter to be outside the body, and preserving a myocardium specimen; where 4-10 pieces of myocardia can be respectively collected from an interventricular septum and free walls of the left ventricle by executing the step 6 and the step 7 repeatedly, in the interval between two adjacent biopsies, heparin saline is used for flushing the guiding catheter and cleaning the myocardial biopsy forcep, and after there is blood flowing out of the guiding catheter, the heparin saline is used for cleaning the myocardial biopsy forcep and flushing the guiding catheter, thereby preventing thrombus and fallen myocardia probably existing in the guiding catheter from being flushed into the left ventricle to cause peripheral artery embolism; and step 8, withdrawing the guiding catheter from the artery sheath through a short guide wire, pulling the artery sheath out of the artery, and performing compression dressing over the access site.

In this embodiment, before the step 8, left ventricle angiography can further be alternately performed, that is, after myocardial biopsies are completed, contrast is injected into the guiding catheter for the left ventricle angiography, thereby making sure whether there is myocardial perforation or not.

By means of the method for performing the coronary angiography and the endomyocardial biopsies in this embodiment, after the catheter is inserted into the blood vessel of the radial artery or ulnar artery, there is no need to insert catheters into blood vessels of other sites in the operation, and there is no need to withdraw the artery sheath from the blood vessel of the artery to be replaced with other sheath catheters or Sheathless guiding catheters neither, so relevant complications caused by stimuli to the puncture site can be reduced, a patient does not need to lie on a bed after the operation and feels more comfortable, and meanwhile, the probability of arteriospasm caused by exchanging the long sheath catheter, the bleeding risk in the replacing process of the sheath catheter and the probability of hematoma of the puncture site and other complications may be reduced; and moreover, the coronary angiography and the myocardial biopsy may be completed by one operation, and "one-stop" interventional diagnosis and treatment of cardiac diseases become possible, which greatly relieves pains of the patient needing to have multiple operations and increases the success rate of operation.

Embodiment 3

This embodiment provides a third implementation of a method for performing cardiology and endovascular interventional operations via a radial artery or ulnar artery of the present invention. The method is a method for performing left ventricle angiography and endomyocardial biopsy in a cardiac interventional operation and includes:

step 1, putting an artery sheath into a punctured artery, wherein the artery is a radial artery or a ulnar artery; wherein before the step 1, conventional sterilization, draping and local anesthesia are firstly performed on a punctured site of the radial artery or ulnar artery of a patient, and then the radial artery or ulnar artery is punctured, wherein whether the radial artery is used or the ulnar artery is used for the operation is determined according to specific conditions of the patient;

step 2, allowing a Pigtail catheter to penetrate into the artery sheath from outside the body and penetrate out of the artery sheath from the other end to be advanced to a left ventricle with the aid of a long guide wire or a short guide wire, and withdrawing the long guide wire or the short guide wire after advancing the Pigtail catheter into the left ventricle, wherein the artery has a small diameter at the puncture site and gradually increases its diameter from the puncture site to the aortic sinus, so the artery sheath does not need to be too long, when the Pigtail catheter penetrates out of the artery sheath from the other end where the diameter of the artery has already been increased, the Pigtail catheter may quite easily penetrate into the left ventricle from the artery at such position, the artery sheath disposed in the artery makes sure that the Pigtail catheter may stably penetrate into the left ventricle, and in this way, the puncture site cannot be continuously stimulated, thereby reducing the probability of vasospasm and increasing the success rate of operation;

step 3, injecting contrast into the Pigtail catheter for left ventricle angiography;

step 4, after completing the left ventricle angiography, advancing the long guide wire into the left ventricle through the Pigtail catheter, withdrawing the Pigtail catheter from the artery sheath, and remaining the long guide wire in the left ventricle, wherein the Pigtail catheter may not continuously stimulate the puncture site when being withdrawn from the artery sheath;

step 5, allowing a guiding catheter to penetrate into the artery sheath from outside the body and penetrate out of the artery sheath from the other end to be advanced to a left ventricle specifically with the aid of the long guide wire remaining in the left ventricle in the step 4, withdrawing the long guide wire and remaining the guiding catheter in the left ventricle, wherein the artery has a small diameter at the puncture site and gradually increases its diameter from the puncture site to the left ventricle, so the artery sheath does not need to be too long, when the guiding catheter penetrates out of one end of the artery sheath disposed in the artery where the diameter of the artery has already been increased, the guiding catheter may quite easily penetrate into the left ventricle from the artery at such position, the artery sheath disposed in the artery makes sure that the guiding catheter may stably penetrate into the left ventricle, and in this way, the puncture site is not continuously stimulated, thereby reducing the probability of vasospasm and increasing the success rate of operation;

step 6, advancing a myocardial biopsy forcep to a left ventricle endocardium through the guiding catheter to collect a piece of myocardium; specifically, adjusting the position of the myocardial biopsy forcep in perspective, withdrawing the myocardial biopsy forcep by about 1.0 cm, opening a punch, advancing the myocardial biopsy forcep back to the left ventricle endocardium, once feeling resistance, rapidly closing the punch, and stably withdrawing the myocardial biopsy forcep to get away from a left ventricle wall while guaranteeing that the punch is in a closed state; wherein before the step 6, the myocardial biopsy forcep are wiped with a heparin saline gauze, in the above process, the position of the guiding catheter can be adjusted such that the myocardial biopsy forcep can reach different positions to take myocardia, and the guiding catheter cannot continuously simulate a puncture site, thereby further reducing the probability of vasospasm and increasing the success rate of operation;

step 7, withdrawing the myocardial biopsy forcep from the guiding catheter to be outside the body, and preserving a myocardium specimen; wherein 4-10 pieces of myocardia can be respectively collected from an interventricular septum and free walls of the left ventricle by executing the step 6 and the step 7 repeatedly, in the interval between two adjacent biopsies, heparin saline is used for flushing the guiding catheter and cleaning the myocardial biopsy forcep, and after there is blood flowing out of the guiding catheter, the heparin saline is used for cleaning the myocardial biopsy forcep and flushing the guiding catheter, thereby preventing thrombus and fallen myocardia probably existing in the guiding catheter from being flushed into the left ventricle to cause peripheral artery embolism; and step 8, withdrawing the guiding catheter from the artery sheath through a short guide wire, pulling the artery sheath out of the artery, and performing compression dressing over the access site.

In this embodiment, before the step 8, left ventricle angiography can further be alternately performed, that is, after myocardial biopsies are completed, contrast is injected into the guiding catheter for the left ventricle angiography, thereby making sure whether there is myocardial perforation or not.

By means of the method for performing the left ventricle angiography and the endomyocardial biopsy in this embodiment, after the catheter is inserted into the blood vessel of the radial artery or ulnar artery, there is no need to insert catheters into blood vessels of other sites in the operation, and there is no need to withdraw the artery sheath from the blood vessel of the artery to be replaced with other sheath catheters or Sheathless guiding catheters neither, so relevant complications caused by stimuli to the puncture site can be reduced, a patient does not need to lie on a bed after the operation and feels more comfortable, and meanwhile, the probability of arteriospasm caused by replacing the long sheath catheter, the bleeding risk in the replacing process of the sheath catheter and the probability of hematoma of the puncture site and other complications may be reduced; and moreover, the left ventricle angiography and the myocardial biopsy may be completed by one operation, and "one-stop" interventional diagnosis and treatment of cardiac diseases become possible, which greatly relieves pains of the patient needing to have multiple operations and increases the success rate of operation.

Embodiment 4

This embodiment provides a fourth implementation of a method for performing cardiology and endovascular interventional operations via a radial artery or ulnar artery of the present invention. The method is a method for performing coronary angiography, left ventricle angiography and endomyocardial biopsy in a cardiac interventional operation and includes:

step 1, putting an artery sheath into a punctured artery, wherein the artery is a radial artery or a ulnar artery; wherein before the step 1, conventional sterilization, draping and local anesthesia are firstly performed on a punctured site of the radial artery or ulnar artery of a patient, and then the radial artery or ulnar artery is punctured, wherein whether the radial artery is used or the ulnar artery is used for the operation is determined according to specific conditions of the patient;

step 2, allowing an angiography catheter to penetrate into the artery sheath from outside the body and penetrate out of the artery sheath from the other end through a short guide wire to be advanced to an aortic sinus, and withdrawing the short guide wire, wherein the artery has a small diameter at the puncture site and gradually increases its diameter from the puncture site to the aortic sinus, so the artery sheath does not need to be too long, when the angiography catheter penetrates out of the artery sheath from the other end where the diameter of the artery has already been increased, the angiography catheter may quite easily penetrate into the aortic sinus from the artery at such position, the artery sheath disposed in the artery makes sure that the angiography catheter may stably penetrate into the aortic sinus, and in this way, the puncture site cannot be continuously stimulated, thereby reducing the probability of vasospasm and increasing the success rate of operation;

step 3, adjusting the angiography catheter to left and right coronary ostia respectively, and injecting contrast into the angiography catheter for coronary angiography;

step 4, after completing the coronary angiography, withdrawing the angiography catheter from the coronary ostia, and allowing the short guide wire to penetrate into the angiography catheter from an in-vitro end and penetrate out of the angiography catheter from the other end located in the artery so as to withdraw the angiography catheter from the artery sheath and remain the short guide wire in the artery, wherein the angiography catheter may not continuously stimulate the puncture site when being withdrawn from the artery sheath;

step 5, allowing a Pigtail catheter to penetrate into the artery sheath from outside the body and penetrate out of the artery sheath from the other end to be advanced to a left ventricle through a short guide wire remaining in the artery in the step 4, and withdrawing the short guide wire after advancing the Pigtail catheter into the left ventricle with the aid of the short guide wire, wherein the artery has a small diameter at the puncture site and gradually increases its diameter from the puncture site to the aortic sinus, so the artery sheath does not need to be too long, when the Pigtail catheter penetrates out of the artery sheath from the other end where the diameter of the artery has already been increased, the Pigtail catheter may quite easily penetrate into the left ventricle from the artery at such position, the artery sheath disposed in the artery makes sure that the Pigtail catheter may stably penetrate into the left ventricle, and in this way, the puncture site cannot be continuously stimulated, thereby reducing the probability of vasospasm and increasing the success rate of operation;

step 6, injecting contrast into the Pigtail catheter for left ventricle angiography;

step 7, after completing the left ventricle angiography, advancing the long guide wire into the left ventricle through the Pigtail catheter, withdrawing the Pigtail catheter from the artery sheath, and remaining the long guide wire in the left ventricle, wherein the Pigtail catheter may not continuously stimulate the puncture site when being withdrawn from the artery sheath;

step 8, allowing a guiding catheter to penetrate into the artery sheath from outside the body and penetrate out of the artery sheath from the other end to reach a left ventricle specifically with the aid of the long guide wire remaining in the left ventricle in the step 7, withdrawing the long guide wire and remaining the guiding catheter in the left ventricle, wherein the artery has a small diameter at the puncture site and gradually increases its diameter from the puncture site to the left ventricle, so the artery sheath does not need to be too long, when the guiding catheter penetrates out of one end of the artery sheath disposed in the artery where the diameter of the artery has already been increased, the guiding catheter may quite easily penetrate into the left ventricle from the artery at such position, the artery sheath disposed in the artery makes sure that the guiding catheter may stably penetrate into the left ventricle, and in this way, the puncture site cannot be continuously stimulated, thereby reducing the probability of vasospasm and increasing the success rate of operation;

step 9, advancing a myocardial biopsy forcep to a left ventricle endocardium through the guiding catheter to collect a piece of myocardium; specifically, adjusting the position of the myocardial biopsy forcep in perspective, withdrawing the myocardial biopsy forcep by about 1.0 cm, opening a punch, advancing the myocardial biopsy forcep back to the left ventricle endocardium, once feeling resistance, rapidly closing the punch, and stably withdrawing the myocardial biopsy forcep to get away from a left ventricle wall while guaranteeing that the punch is in a closed state; wherein before the step 9, the myocardial biopsy forcep are wiped with a heparin saline gauze, in the above process, the position of the guiding catheter can be adjusted such that the myocardial biopsy forcep can reach different positions to take myocardia, and the guiding catheter cannot continuously simulate a puncture site, thereby further reducing the probability of vasospasm and increasing the success rate of operation;

step 10, withdrawing the myocardial biopsy forcep from the guiding catheter to be outside the body, and preserving a myocardium specimen; wherein 4-10 pieces of myocardia can be respectively collected from an interventricular septum and free walls of the left ventricle by executing the step 9 and the step 10 repeatedly, in the interval between two adjacent biopsies, heparin saline is used for flushing the guiding catheter and cleaning the myocardial biopsy forcep, and after there is blood flowing out of the guiding catheter, the heparin saline is used for cleaning the myocardial biopsy forcep and flushing the guiding catheter, thereby preventing thrombus and fallen myocardia probably existing in the guiding catheter from being flushed into the left ventricle to cause peripheral artery embolism; and step 11, withdrawing the guiding catheter from the artery sheath through a short guide wire, pulling the artery sheath out of the artery, and performing compression dressing over the access site.

In this embodiment, before the step 11, left ventricle angiography can further be alternately performed, that is, after a myocardial biopsy is completed, contrast is injected into the guiding catheter for the left ventricle angiography, thereby avoiding myocardial perforation and other complications.

By means of the method for performing the coronary angiography, the left ventricle angiography and the endomyocardial biopsy in this embodiment, after the catheter is inserted into the blood vessel of the radial artery or ulnar artery, there is no need to insert catheters into blood vessels of other sites in the operation, and there is no need to withdraw the artery sheath from the blood vessel of the artery to be replaced with other sheath catheters neither, so relevant complications caused by stimuli to the puncture site can be reduced, a patient does not need to lie on a bed after the operation and feels more comfortable, and meanwhile, the probability of arteriospasm caused by replacing the long sheath catheter, the bleeding risk in the replacing process of the sheath catheter and the probability of hematoma of the puncture site and other complications may be reduced; and moreover, the coronary angiography, the left ventricle angiography and the myocardial biopsy may be completed by one operation, and "one-stop" interventional diagnosis and treatment of cardiac diseases become possible, which greatly relieves pains of the patient needing to have multiple operations and increases the success rate of operation.

In other embodiments, it is feasible to perform the left ventricle angiography in the steps 5-7 and then perform the coronary angiography in the steps 2-4.

Embodiment 5

This embodiment provides a fifth implementation of a method for performing cardiology and endovascular interventional operations via a radial artery or ulnar artery of the present invention. The method is a method for performing a coronary interventional therapy operation and an endomyocardial biopsy in a cardiac interventional operation and includes:

step 1, putting an artery sheath into a punctured artery, wherein the artery is a radial artery or a ulnar artery; wherein before the step 1, conventional sterilization, draping and local anesthesia are firstly performed on a punctured site of the radial artery or ulnar artery of a patient, and then the radial artery or ulnar artery is punctured, wherein whether the radial artery is used or the ulnar artery is used for the operation is determined according to specific conditions of the patient;

step 2, allowing a guiding catheter to penetrate into the artery sheath from outside the body and penetrate out of the artery sheath from the other end through a short guide wire to be advanced to an aortic sinus, and withdrawing the short guide wire, wherein the artery has a small diameter at the puncture site and gradually increases its diameter from the puncture site to the aortic sinus, so the artery sheath does not need to be too long, when the angiography catheter penetrates out of the artery sheath from the other end where the diameter of the artery has already been increased, the angiography catheter may quite easily penetrate into the aortic sinus from the artery at such position, the artery sheath disposed in the artery makes sure that the angiography catheter may stably penetrate into the aortic sinus, and in this way, the puncture site cannot be continuously stimulated, thereby reducing the probability of vasospasm and increasing the success rate of operation;

step 3, injecting contrast through the guiding catheter for coronary angiography, and/or allowing a coronary interventional therapy apparatus to enter through the guiding catheter for a coronary interventional therapy operation;

step 4, after completing the coronary angiography or the coronary interventional therapy operation, withdrawing the guiding catheter from a coronary ostium, allowing a short guide wire to penetrate into the guiding catheter from an in-vitro end and penetrate out of the guiding catheter from the other end located in the artery, advancing the guiding catheter into a left ventricle with the aid of the short guide wire, withdrawing the short guide wire, and remaining the guiding catheter in the left ventricle;

step 5, advancing a myocardial biopsy forcep through the guiding catheter to a left ventricle endocardium to collect a piece of myocardium; specifically, adjusting the position of the myocardial biopsy forcep in perspective, withdrawing the myocardial biopsy forcep by about 1.0 cm, opening a punch, advancing the myocardial biopsy forcep back to the left ventricle endocardium, once feeling resistance, rapidly closing the punch, and stably withdrawing the myocardial biopsy forcep to get away from a left ventricle wall while guaranteeing that the punch is in a closed state; wherein before the step 5, the myocardial biopsy forcep are wiped with a heparin saline gauze, in the above process, the position of the guiding catheter can be adjusted such that the myocardial biopsy forcep can reach different positions to take myocardia, and the guiding catheter does not continuously simulate a puncture site, thereby further reducing the probability of vasospasm and increasing the success rate of operation;

step 6, withdrawing the myocardial biopsy forcep from the guiding catheter to be outside the body, and preserving a myocardium specimen; where 4-10 pieces of myocardia can be respectively collected from an interventricular septum and free walls of the left ventricle by executing the step 5 and the step 6 repeatedly, in the interval between two adjacent biopsies, heparin saline is used for flushing the guiding catheter and cleaning the myocardial biopsy forcep, and after there is blood flowing out of the guiding catheter, the heparin saline is used for cleaning the myocardial biopsy forcep and flushing the guiding catheter, thereby preventing thrombus and fallen myocardia probably existing in the guiding catheter from being flushed into the left ventricle to cause peripheral artery embolism;

step 7, after completing a myocardial biopsy, using the guiding catheter for the left ventricle angiography, thereby making sure whether there is myocardial perforation or not; and step 8, withdrawing the guiding catheter from the artery sheath through a short guide wire, pulling the artery sheath out of the artery, and performing compression dressing over the access site.

In this embodiment, before the step 8, left ventricle angiography can further be alternately performed, that is, after a myocardial biopsy is completed, contrast is injected into the guiding catheter for the left ventricle angiography, thereby making sure whether there is myocardial perforation or not.

By means of the method for performing the coronary angiography or coronary interventional therapy operation and the endomyocardial biopsy in this embodiment, after the catheter is inserted into the blood vessel of the radial artery or ulnar artery, there is no need to insert catheters into blood vessels of other sites in the operation, and there is no need to withdraw the artery sheath from the blood vessel of the artery to be replaced with other sheath catheters neither, so relevant complications caused by stimuli to the puncture site can be reduced, a patient does not need to lie on a bed after the operation and feels more comfortable, and meanwhile, the probability of arteriospasm caused by replacing the long sheath catheter, the bleeding risk in the replacing process of the sheath catheter and the probability of hematoma of the puncture site and other complications may be reduced; and moreover, the coronary interventional therapy and the myocardial biopsies can be completed through one guiding catheter by one operation, which is particularly suitable for the coronary interventional therapy and the endomyocardial biopsy, and "one-stop" interventional diagnosis and treatment of cardiac diseases become possible, which saves medical costs, greatly relieves pains of the patient needing to have multiple operations and increases the success rate of operation.

Embodiment 6

This example as shown in FIGS. 1-7 provides a first implementation of a device for performing cardiology and endovascular interventional operations via a radial artery or ulnar artery of the present invention. The device includes an artery sheath 1 connected to a hemostasis valve 11, a guiding catheter 2, myocardial biopsy forcep 3, an angiography catheter 4, a Pigtail catheter 12, a Y-shaped hemostasis valve 5, a pressure transducer 6, a pressure monitor 7, a three-way stopcock 8, contrast injection system 9, a long guide wire and a short guide wire, wherein the artery sheath 1 is configured to be put into a punctured artery of the radial artery or ulnar artery, the guiding catheter 2, the angiography catheter 4 and the Pigtail catheter 12 can respectively penetrate out of the artery sheath 1 into the artery, the angiography catheter 4 can be advanced to an aortic sinus, the guiding catheter 2 and the Pigtail catheter 12 can be advanced to an aorta, a peripheral artery, an aortic sinus or/and a left ventricle, and the myocardial biopsy forcep 3 can penetrate out of the guiding catheter 2 to enter the left ventricle and are configured to punch a myocardium. The head end of a catheter is bent at an angle and may be straightened after the long guide wire or the short guide wire is disposed therein, so that the injury probability of a blood vessel where the catheter enters is reduced. In figures, the contrast injection system 9 only shows a schematic form, which does not represent its true form.

Figure 3:
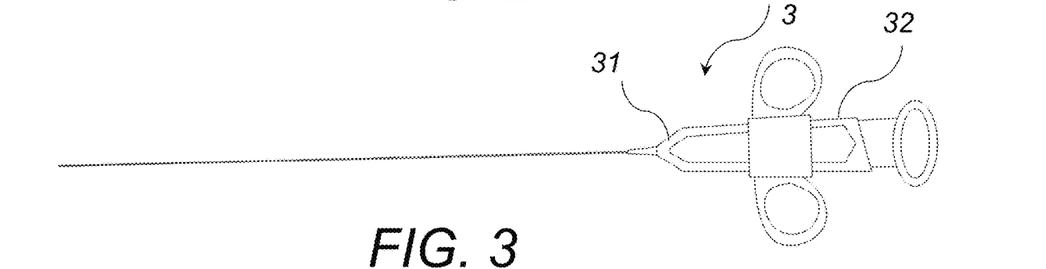
FIG. 3 is a structural schematic diagram of myocardial biopsy forcep in an embodiment of the present invention.

The Y-shaped hemostasis valve 5 includes three ports 5a, 5b, 5c communicating with one another, wherein the first port 5a of the Y-shaped hemostasis valve 5 linearly communicates with the second port 5b of the Y-shaped hemostasis valve 5, and a hemostasis valve body 10 is disposed at the second port 5b of the Y-shaped hemostasis valve 5. The myocardial biopsy forcep 3 include a punch at the front end and a forcep body 31 at the rear end.

The device in this embodiment can be adopted to perform all operations in embodiments 1-5, wherein the operation in each embodiment only selectively adopts some of the above parts. The specific use conditions of the parts are shown as follows:

When the myocardial biopsy in Embodiment 1 is performed, the device of this embodiment is adopted for the operation as follows:

The artery sheath 1 is put into the blood vessel after conventional sterilization, draping and local anesthesia are performed on the puncture site of the radial artery of a patient and the radial artery is punctured.

Figure 2:
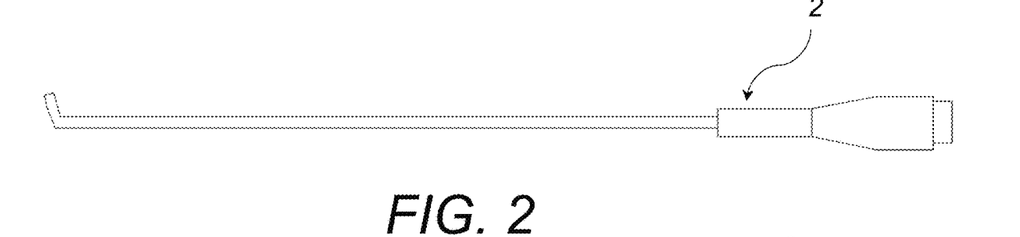
FIG. 2 is a structural schematic diagram of a guiding catheter in an embodiment of the present invention.

The guiding catheter 2 is advanced into a left ventricle through the short guide wire, the short guide wire is withdrawn, and the guiding catheter 2 remains in the left ventricle.

Figure 7:
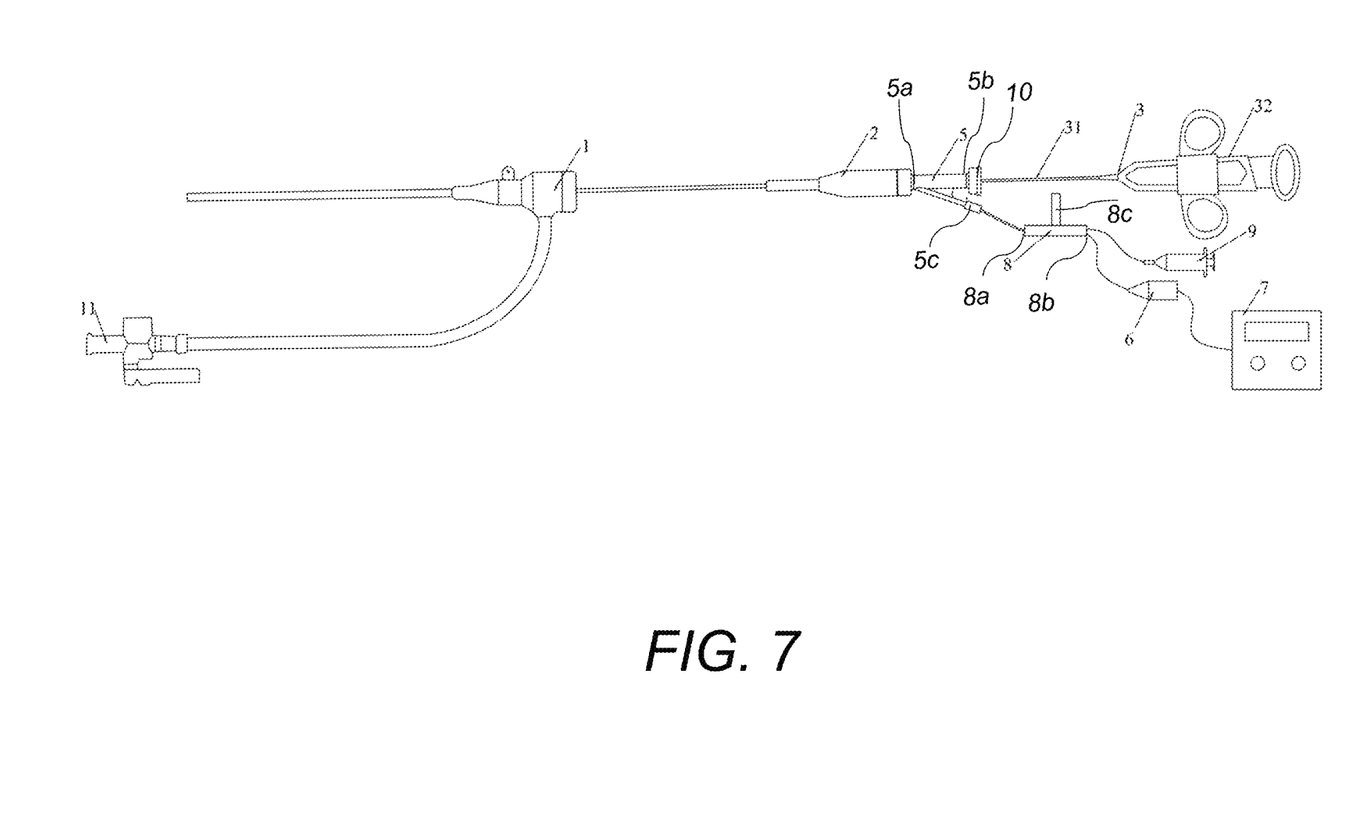
FIG. 7 is a structural schematic diagram of connection in myocardial biopsy in an embodiment of the present invention.

The first port 5a of the Y-shaped hemostasis valve 5 communicates with an in-vitro port of the guiding catheter 2, and the myocardial biopsy forcep penetrate into the Y-shaped hemostasis valve 5 and the guiding catheter 2 from the second port 5b of the Y-shaped hemostasis valve 5. A first port 8a of the three-way stopcock 8 communicates with the third port 5c of the Y-shaped hemostasis valve 5, a second port 8b of the three-way stopcock 8 is connected with the pressure transducer 6 and the contrast injection system 9. The pressure transducer 6 and the pressure monitor 7 are configured to measure a blood pressure value in an operation. The contrast injection system 9 is configured to inject a small amount of contrast into a left ventricle to confirm that a port hole of the guiding catheter 2 is located in the ventricle but not abut against a ventricle wall.

A third port 8c of the three-way stopcock 8 is configured to exhaust gas before an operation, after exhausting, a rotary switch on the three-way stopcock 8 is adjusted to close the third port 8c and to communicate the first port 8a with the second port 8b, and then the myocardial biopsy is performed.

After the myocardial biopsy forcep 3 are wiped with the heparin saline gauze, the punch and the forcep body 31 of the myocardial biopsy forcep 3 penetrate into the Y-shaped hemostasis valve 5 and the guiding catheter 2 from the second port of the Y-shaped hemostasis valve 5, as shown in FIG. 7. The myocardial biopsy forcep 3 are advanced to a left ventricle endocardium, the position of the myocardial biopsy forcep 3 is adjusted in perspective, the myocardial biopsy forcep 3 are withdrawn by about 1.0 cm, a punch is opened, the myocardial biopsy forcep 3 are advanced back to the left ventricle endocardium, once resistance is felt, the punch is rapidly closed, and the myocardial biopsy forcep 3 are stably withdrawn to get away from a left ventricle wall while it is guaranteed that the punch is in a closed state.

The jaw of the myocardial biopsy forcep 3 is opened after the myocardial biopsy forcep 3 are withdrawn from the guiding catheter 2 to be outside the body, and a myocardium specimen therein is preserved. 4-10 pieces of myocardia can be respectively collected from an interventricular septum and free walls of the left ventricle by executing the above steps repeatedly, in the interval between two adjacent biopsies, the hemostasis valve body 10 at the second port 5b of the Y-shaped hemostasis valve is switched on, and after there is blood flowing out visibly, heparin saline is used for flushing the guiding catheter 2, then the second port 5b of the Y-shaped hemostasis valve is switched off to stop bleeding, and cleaning the myocardial biopsy forcep 3, thereby preventing thrombus and fallen myocardia probably existing in the guiding catheter from being flushed into the left ventricle to cause peripheral artery embolism. After the operation ends, the hemostasis valve body 10 at the second port 5b of the Y-shaped hemostasis valve 5 is switched on, and after there is blood flowing out visibly, the heparin saline is used for cleaning the myocardial biopsy forcep 3 and flushing the guiding catheter 2, thereby preventing thrombus and fallen myocardia probably existing in the guiding catheter from being flushed into the left ventricle to cause peripheral artery embolism.

After the operation ends, the guiding catheter 2 is withdrawn through the short guide wire, then the artery sheath 1 is pulled out of the radial artery, and local pressure dressing is performed.

When the coronary angiography and the myocardial biopsy in Embodiment 2 are performed, the device of this embodiment is adopted for the operation as follows:

The artery sheath 1 is put into the blood vessel after conventional sterilization, draping and local anesthesia are performed on the puncture site of the radial artery of a patient and the radial artery is punctured.

Figure 4:
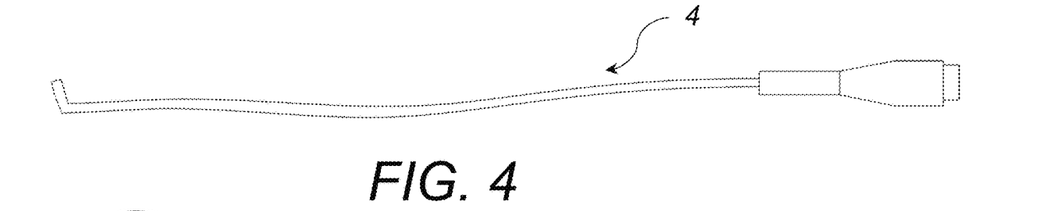
FIG. 4 is a structural schematic diagram of an angiography catheter in an embodiment of the present invention.

The angiography catheter 4 is allowed to penetrate into the artery sheath from outside the body and penetrate out of the artery sheath from the other end through the short guide wire to be advanced to an aortic sinus, and the short guide wire is withdrawn.

Figure 6:
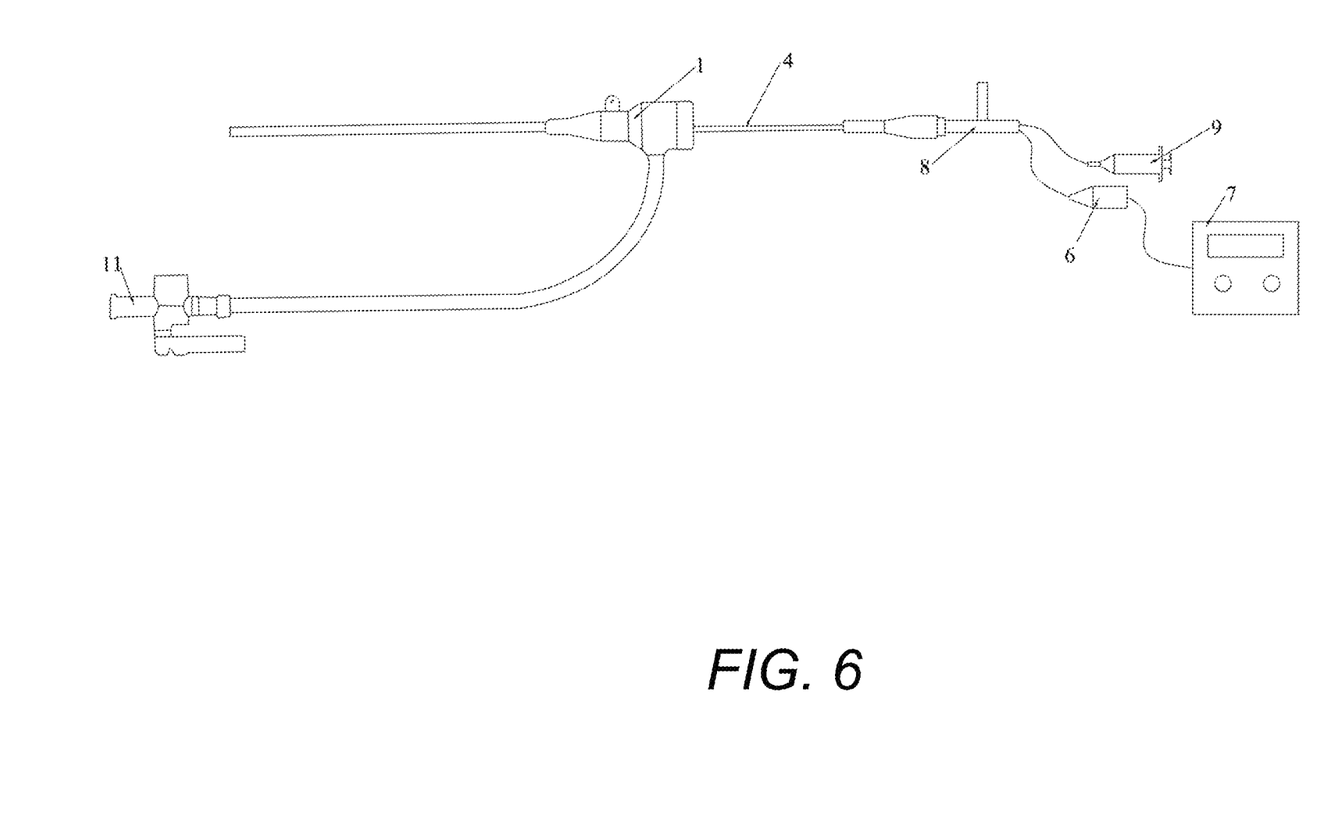
FIG. 6 is a structural schematic diagram of connection in coronary angiography in an embodiment of the present invention.

The tail end of the angiography catheter 4 communicates with the first port 8a of the three-way stopcock 8, and the second port 8b of the three-way stopcock 8 is connected with the pressure transducer 6 and the contrast injection system 9. The pressure transducer 6 and the pressure monitor 7 are connected and are configured to detect a blood pressure value in an operation. The contrast injection system 9 is configured to inject contrast. The third port 8c of the three-way stopcock 8 is configured to exhaust gas before an operation. After exhausting, the rotary switch on the three-way stopcock 8 is adjusted to close the third port 8c of the three-way stopcock 8 and communicate the first port 8a with the second port 8b, and then the coronary angiography is performed, as shown in FIG. 6.

After the coronary angiography is completed, the angiography catheter is withdrawn from a coronary ostium, and the short guide wire penetrates into the angiography catheter from an in-vitro end and penetrates out of the angiography catheter from the other end located in the artery so as to withdraw the angiography catheter 4 from the artery sheath as well and remain the short guide wire in the artery.

The guiding catheter 2 is advanced into a left ventricle through the short guide wire, the short guide wire is withdrawn, and the guiding catheter 2 remains in the left ventricle.

The first port of the Y-shaped hemostasis valve 5 communicates with an in-vitro port of the guiding catheter 2, and the myocardial biopsy forcep penetrate into the Y-shaped hemostasis valve 5 and the guiding catheter 2 from the second port of the Y-shaped hemostasis valve 5. A first port of the three-way stopcock 8 communicates with the third port of the Y-shaped hemostasis valve 5, a second port of the three-way stopcock 8 is connected with the pressure transducer 6 and the contrast injection system 9. The pressure transducer 6 and the pressure monitor 7 are configured to measure a blood pressure value in an operation. The contrast injection system 9 is configured to inject a small amount of contrast into a left ventricle to confirm that a port hole of the guiding catheter 2 is located in the ventricle but not abut against a ventricle wall.

A third port of the three-way stopcock 8 is configured to exhaust gas before an operation, after exhausting, a rotary switch on the three-way stopcock 8 is adjusted to close the third port and to communicate the first port with the second port, and then the myocardial biopsy is performed.

After the myocardial biopsy forcep 3 are wiped with the heparin saline gauze, the punch and the forcep body 31 of the myocardial biopsy forcep 3 penetrate into the Y-shaped hemostasis valve 5 and the guiding catheter 2 from the second port of the Y-shaped hemostasis valve 5, as shown in FIG. 7. The myocardial biopsy forcep 3 are advanced to a left ventricle endocardium, the position of the myocardial biopsy forcep 3 is adjusted in perspective, the myocardial biopsy forcep 3 are withdrawn by about 1.0 cm, a punch is opened, the myocardial biopsy forcep 3 are advanced back to the left ventricle endocardium, once resistance is felt, the punch is rapidly closed, and the myocardial biopsy forcep 3 are stably withdrawn to get away from a left ventricle wall while it is guaranteed that the punch is in a closed state.

The jaw of the myocardial biopsy forcep 3 is opened after the myocardial biopsy forcep 3 are withdrawn from the guiding catheter 2 to be outside the body, and a myocardium specimen therein is preserved. 4-10 pieces of myocardia can be respectively collected from an interventricular septum and free walls of the left ventricle by executing the above steps repeatedly, in the interval between two adjacent biopsies, the hemostasis valve body 10 at the second port 5b of the Y-shaped hemostasis valve 5 is switched on, and after there is blood flowing out visibly, thrombus and fallen myocardia probably existing in the guiding catheter are prevented from being flushed into the left ventricle to cause peripheral artery embolism. The heparin saline is used for flushing the guiding catheter 2 and cleaning the myocardial biopsy forcep 3. After the operation ends, the hemostasis valve body 10 at the second port 5b of the Y-shaped hemostasis valve 5 is switched on, and after there is blood flowing out visibly, thrombus and fallen myocardia probably existing in the guiding catheter are prevented from being flushed into the left ventricle to cause peripheral artery embolism. The heparin saline is used for cleaning the myocardial biopsy forcep 3 and flushing the guiding catheter 2. After the operation ends, the guiding catheter 2 is withdrawn through a first guide wire, then the artery sheath 1 is pulled out of the radial artery, and local pressure dressing is performed.

When the left ventricle angiography and the myocardial biopsy in Embodiment 3 are performed, the device of this embodiment is adopted for the operation as follows:

The artery sheath 1 is put into the blood vessel after conventional sterilization, draping and local anesthesia are performed on the puncture site of the radial artery of a patient and the radial artery is punctured.

Figure 5:
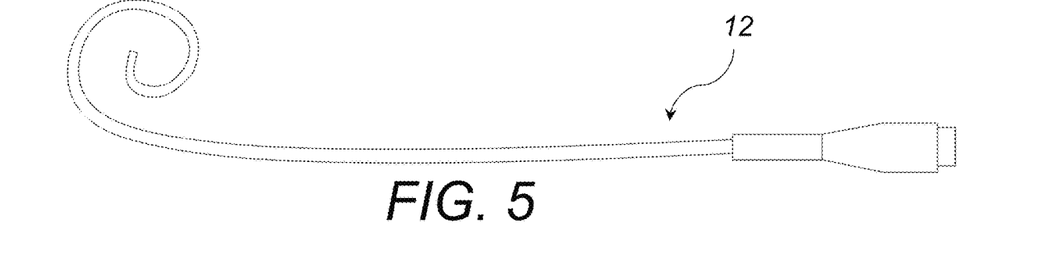
FIG. 5 is a structural schematic diagram of a Pigtail catheter in an embodiment of the present invention.

The Pigtail catheter 12 is allowed to penetrate into the artery sheath 1 in vitro and penetrate out of the artery sheath 1 from the other end through the short guide wire to be advanced to a left ventricle, and the short guide wire is withdrawn.

The tail end of the Pigtail catheter communicates with the first port of the three-way stopcock 8, and the second port of the three-way stopcock 8 is connected with the pressure transducer 6 and the contrast injection system 9. The pressure transducer 6 and the pressure monitor 7 are connected and are configured to detect a blood pressure value port of the three-way stopcock 8 is configured to exhaust gas before an operation. After exhausting, the rotary switch on the three-way stopcock 8 is adjusted to close the third port of the three-way stopcock 8 and communicate the first port with the second port, and then the left ventricle angiography is performed.

After the left ventricle angiography is completed, the long guide wire penetrates into the Pigtail catheter from an in-vitro end and penetrates out of the Pigtail catheter from the other end, the Pigtail catheter is withdrawn, and the long guide wire remains in the left ventricle.

The guiding catheter 2 is advanced into the left ventricle through the long guide wire, the long guide wire is withdrawn, and the guiding catheter 2 remains in the left ventricle.

The first port of the Y-shaped hemostasis valve 5 communicates with an in-vitro port of the guiding catheter 2, and the myocardial biopsy forcep penetrate into the Y-shaped hemostasis valve 5 and the guiding catheter 2 from the second port of the Y-shaped hemostasis valve 5. A first port of the three-way stopcock 8 communicates with the third port of the Y-shaped hemostasis valve 5, and a second port of the three-way stopcock 8 is connected with the pressure transducer 6 and the contrast injection system 9. The pressure transducer 6 and the pressure monitor 7 are configured to measure a blood pressure value in an operation. The contrast injection system 9 is configured to inject a small amount of contrast into a left ventricle to confirm that a port hole of the guiding catheter 2 is located in the ventricle but not abut against a ventricle wall.

A third port of the three-way stopcock 8 is configured to exhaust gas before an operation, after exhausting, a rotary switch on the three-way stopcock 8 is adjusted to close the third port and to communicate the first port with the second port, and then the myocardial biopsy is performed.

After the myocardial biopsy forcep 3 are wiped with the heparin saline gauze, the punch and the forcep body 31 of the myocardial biopsy forcep 3 penetrate into the Y-shaped hemostasis valve 5 and the guiding catheter 2 from the second port of the Y-shaped hemostasis valve 5, as shown in FIG. 7. The myocardial biopsy forcep 3 are advanced to a left ventricle endocardium, the position of the myocardial biopsy forcep 3 is adjusted in perspective, the myocardial biopsy forcep 3 are withdrawn by about 1.0 cm, a punch is opened, the myocardial biopsy forcep 3 are advanced back to the left ventricle endocardium, once resistance is felt, the punch is rapidly closed, and the myocardial biopsy forcep 3 are stably withdrawn to get away from a left ventricle wall while it is guaranteed that the punch is in a closed state.

The jaw of the myocardial biopsy forcep 3 is opened after the myocardial biopsy forcep 3 are withdrawn from the guiding catheter 2 to be outside the body, and a myocardium specimen therein is preserved. 4-10 pieces of myocardia can be respectively collected from an interventricular septum and free walls of the left ventricle by executing the above steps repeatedly, in the interval between two adjacent biopsies, the hemostasis valve body at the second port of the Y-shaped hemostasis valve is switched on, and after there is blood flowing out visibly, thrombus and fallen myocardia probably existing in the guiding catheter are prevented from being flushed into the left ventricle to cause peripheral artery embolism. The heparin saline is used for flushing the guiding catheter 2 and cleaning the myocardial biopsy forcep 3. After the operation ends, the hemostasis valve body at the second port of the Y-shaped hemostasis valve is switched on, and after there is blood flowing out visibly, thrombus and fallen myocardia probably existing in the guiding catheter are prevented from being flushed into the left ventricle to cause peripheral artery embolism. The heparin saline is used for cleaning the myocardial biopsy forcep 3 and flushing the guiding catheter 2. After the operation ends, the guiding catheter 2 is withdrawn through a first guide wire, then the artery sheath 1 is pulled out of the radial artery, and local pressure dressing is performed.

When the coronary angiography, the left ventricle angiography and the myocardial biopsy in Embodiment 4 are performed, the device of this embodiment is adopted for the operation as follows:

The artery sheath 1 is put into the blood vessel after conventional sterilization, draping and local anesthesia are performed on the puncture site of the radial artery of a patient and the radial artery is punctured.

The angiography catheter 4 is allowed to penetrate into the artery sheath from outside the body and penetrate out of the artery sheath from the other end through the short guide wire to be advanced to an aortic sinus, and the short guide wire is withdrawn.

The tail end of the angiography catheter 4 communicates with the first port of the three-way stopcock 8, and the second port of the three-way stopcock 8 is connected with the pressure transducer 6 and the contrast injection system 9. The pressure transducer 6 and the pressure monitor 7 are connected and are configured to detect a blood pressure value port of the three-way stopcock 8 is configured to exhaust gas before an operation. After exhausting, the rotary switch on the three-way stopcock 8 is adjusted to close the third port of the three-way stopcock 8 and communicate the first port with the second port, and then the coronary angiography is performed, as shown in FIG. 6.

After the coronary angiography is completed, the angiography catheter 4 is withdrawn from a coronary ostium, and the short guide wire penetrates into the angiography catheter 4 from an in-vitro end and penetrates out of the angiography catheter from the other end so as to withdraw the angiography catheter 4 from the artery sheath 1 as well and remain the short guide wire in the artery.

The Pigtail catheter is allowed to penetrate into the artery sheath from outside the body and penetrate out of the artery sheath from the other end through the short guide wire to be advanced to a left ventricle with the aid of the short guide wire, and the short guide wire is withdrawn.

The tail end of the Pigtail catheter communicates with the first port of the three-way stopcock 8, and the second port of the three-way stopcock 8 is connected with the pressure transducer 6 and the contrast injection system 9. The pressure transducer 6 and the pressure monitor 7 are connected and are configured to detect a blood pressure value in an operation. The contrast injection system 9 is configured to inject contrast. The third port of the three-way stopcock 8 is configured to exhaust gas before an operation. After exhausting, the rotary switch on the three-way stopcock 8 is adjusted to close the third port of the three-way stopcock 8 and communicate the first port with the second port, and then the left ventricle angiography is performed.

After the left ventricle angiography is completed, the long guide wire is advanced into the left ventricle through the Pigtail catheter, the Pigtail catheter is withdrawn, the long guide wire remains in the left ventricle, the guiding catheter 2 is advanced into the left ventricle along the long guide wire, the long guide wire is withdrawn, and the guiding catheter 2 remains in the left ventricle.

The first port of the Y-shaped hemostasis valve 5 communicates with an in-vitro port of the guiding catheter 2, and the myocardial biopsy forcep penetrate into the Y-shaped hemostasis valve 5 and the guiding catheter 2 from the second port of the Y-shaped hemostasis valve 5. A first port of the three-way stopcock 8 communicates with the third port of the Y-shaped hemostasis valve 5, and a second port of the three-way stopcock 8 is connected with the pressure transducer 6 and the contrast injection system 9. The pressure transducer 6 and the pressure monitor 7 are configured to measure a blood pressure value in an operation. The contrast injection system 9 is configured to inject a small amount of contrast into a left ventricle to confirm that a port hole of the guiding catheter 2 is located in the ventricle but not abut against a ventricle wall.

A third port of the three-way stopcock 8 is configured to exhaust gas before an operation, after exhausting, a rotary switch on the three-way stopcock 8 is adjusted to close the third port and to communicate the first port with the second port, and then the myocardial biopsy is performed.

After the myocardial biopsy forcep 3 are wiped with the heparin saline gauze, the punch and the forcep body 31 of the myocardial biopsy forcep 3 penetrate into the Y-shaped hemostasis valve 5 and the guiding catheter 2 from the second port of the Y-shaped hemostasis valve 5, as shown in FIG. 7. The myocardial biopsy forcep 3 are advanced to a left ventricle endocardium, the position of the myocardial biopsy forcep 3 is adjusted in perspective, the myocardial biopsy forcep 3 are withdrawn by about 1.0 cm, a punch is opened, the myocardial biopsy forcep 3 are advanced back to the left ventricle endocardium, once resistance is felt, the punch is rapidly closed, and the myocardial biopsy forcep 3 are stably withdrawn to get away from a left ventricle wall while it is guaranteed that the punch is in a closed state.

The jaw of the myocardial biopsy forcep 3 is opened after the myocardial biopsy forcep 3 are withdrawn from the guiding catheter 2 to be outside the body, and a myocardium specimen therein is preserved. 4-10 pieces of myocardia can be respectively collected from an interventricular septum and free walls of the left ventricle by executing the above steps repeatedly, in the interval between two adjacent biopsies, the hemostasis valve body at the second port of the Y-shaped hemostasis valve is switched on, and after there is blood flowing out visibly, heparin saline is used for flushing the guiding catheter 2 and cleaning the myocardial biopsy forcep 3, thereby preventing thrombus and fallen myocardia probably existing in the guiding catheter from being flushed into the left ventricle to cause peripheral artery embolism. After the operation ends, the hemostasis valve body at the second port of the Y-shaped hemostasis valve is switched on, and after there is blood flowing out visibly, the heparin saline is used for cleaning the myocardial biopsy forcep 3 and flushing the guiding catheter 2, thereby preventing thrombus and fallen myocardia probably existing in the guiding catheter from being flushed into the left ventricle to cause peripheral artery embolism. After the operation ends, the guiding catheter 2 is withdrawn through the short guide wire, then the artery sheath 1 is pulled out of the radial artery, and local pressure dressing is performed.

When the coronary angiography or coronary interventional therapy and the myocardial biopsy in Embodiment 5 are performed, the device in this embodiment can also be adopted, that is, the coronary interventional therapy and the myocardial biopsy are performed through the same guiding catheter 2 as follows:

The artery sheath 1 is put into the blood vessel after conventional sterilization, draping and local anesthesia are performed on the puncture site of the radial artery of a patient and the radial artery is punctured.

The guiding catheter 2 is allowed to penetrate into the artery sheath from outside the body and penetrate out of the artery sheath from the other end in the artery through the short guide wire to be advanced to an aortic sinus, and the short guide wire is withdrawn.

The first port of the Y-shaped hemostasis valve 5 communicates with the in-vitro port of the guiding catheter 2. The first port of the three-way stopcock 8 communicates with the third port of the Y-shaped hemostasis valve 5, and the second port of the three-way stopcock 8 is connected with the pressure transducer 6 and the contrast injection system 9. The pressure transducer 6 and the pressure monitor 7 are configured to measure a blood pressure value in an operation. The contrast injection system 9 is configured to inject a small amount of contrast into a coronary artery to confirm the position of a coronary artery lesion and the position of the guiding catheter 2.

The third port of the three-way stopcock 8 is configured to exhaust gas before an operation, after exhausting, the rotary switch on the three-way stopcock 8 is adjusted to close the third port and to communicate the first port with the second port, the guiding catheter is adjusted to a left or right coronary ostium according to specific clinical conditions, then contrast may be injected into the guiding catheter for coronary angiography, and a corresponding coronary interventional therapy apparatus may enter through the guiding catheter to complete a coronary interventional therapy operation.

After the coronary interventional therapy is completed, the guiding catheter 2 is withdrawn from the coronary ostium, the short guide wire penetrates into the guiding catheter 2 from an in-vitro end and penetrates out of the guiding catheter from the other end located in the artery, the guiding catheter is advanced into the left ventricle with the aid of the short guide wire, the short guide wire is withdrawn, and the guiding catheter remains in the left ventricle. The first port of the Y-shaped hemostasis valve 5 communicates with an in-vitro port of the guiding catheter 2, and the myocardial biopsy forcep penetrate into the Y-shaped hemostasis valve 5 and the guiding catheter 2 from the second port of the Y-shaped hemostasis valve 5. A first port of the three-way stopcock 8 communicates with the third port of the Y-shaped hemostasis valve 5, and a second port of the three-way stopcock 8 is connected with the pressure transducer 6 and the contrast injection system 9. The pressure transducer 6 and the pressure monitor 7 are configured to measure a blood pressure value in an operation. The contrast injection system 9 is configured to inject a small amount of contrast into a left ventricle to confirm that a port hole of the guiding catheter 2 is located in the ventricle but not abut against a ventricle wall.

A third port of the three-way stopcock 8 is configured to exhaust gas before an operation, after exhausting, a rotary switch on the three-way stopcock 8 is adjusted to close the third port and to communicate the first port with the second port, and then the myocardial biopsy is performed.

After the myocardial biopsy forcep 3 are wiped with the heparin saline gauze, the punch and the forcep body 31 of the myocardial biopsy forcep 3 puncture into the Y-shaped hemostasis valve 5 and the guiding catheter 2 from the second port of the Y-shaped hemostasis valve 5, as shown in FIG. 7. The myocardial biopsy forcep 3 are advanced to a left ventricle endocardium, the position of the myocardial biopsy forcep 3 is adjusted in perspective, the myocardial biopsy forcep 3 are withdrawn by about 1.0 cm, a punch is opened, the myocardial biopsy forcep 3 are advanced back to the left ventricle endocardium, once resistance is felt, the punch is rapidly closed, and the myocardial biopsy forcep 3 are stably withdrawn to get away from a left ventricle wall while it is guaranteed that the punch is in a closed state.

The jaw of the myocardial biopsy forcep 3 is opened after the myocardial biopsy forcep 3 are withdrawn from the guiding catheter 2 to be outside the body, and a myocardium specimen therein is preserved. 4-10 pieces of myocardia can be respectively collected from an interventricular septum and free walls of the left ventricle by executing the above steps repeatedly, in the interval between two adjacent biopsies, the hemostasis valve body at the second port of the Y-shaped hemostasis valve is switched on, and after there is blood flowing out visibly, heparin saline is used for flushing the guiding catheter 2 and cleaning the myocardial biopsy forcep 3, thereby preventing thrombus and fallen myocardia probably existing in the guiding catheter from being flushed into the left ventricle to cause peripheral artery embolism. After the operation ends, the hemostasis valve body at the second port of the Y-shaped hemostasis valve is switched on, and after there is blood flowing out visibly, the heparin saline is used for cleaning the myocardial biopsy forcep 3 and flushing the guiding catheter 2, thereby preventing thrombus and fallen myocardia probably existing in the guiding catheter from being flushed into the left ventricle to cause peripheral artery embolism.

It should be noted that the long guide wire and the short guide wire described in the above embodiments are relative.

The device for performing a cardiac interventional operation via a radial artery or ulnar artery in this embodiment does not need to pull the artery sheath out of the blood vessel in the cardiac interventional operation after puncturing the artery of the radial artery or ulnar artery, thereby preventing a patient from bleeding too much and reducing the probability of hematoma and other complications at a puncture site. The guiding catheter 2 and the myocardial biopsy forcep 3 may not continuously stimulate the puncture site when penetrating into the artery sheath for operation, and the artery sheath 1 has no displacement relative to the puncture site, thereby reducing the probability of corresponding stimuli and vasospasm and increasing the success rate of operation. In addition, an dilator in a previous Sheathless guiding catheter operation device has a sharp head end and may increase the injury probability of blood vessels and cardiac valves if it is improperly operated, but the device provided by the solution may be prevented from such problem because it does not need to use the dilator in a Sheathless guiding catheter technology in an operation. Furthermore, a patient may have coronary angiography, left ventricle angiography and myocardial biopsy in sequence by means of the device in this embodiment and only needs to undergo one time of artery puncture instead of puncturing into other blood vessels, so pains of the patient are greatly relieved, and the success rate of operation is increased.

The combinations of sizes of the artery sheath 1, the guiding catheter 2 and the myocardial biopsy forcep 3 in this embodiment, selected according to specific clinical conditions of a patient, are shown in the table below.

|   | Artery sheath 1 | | | Guiding catheter 2 | | | Myocardial biopsy forceps 3 | |
|---|---|---|---|---|---|---|---|---|
|   | Length/cm | Outer diameter/mm | Inner diameter/mm | Length/cm | Outer diameter/mm | Inner diameter/mm | Length/cm | Outer diameter/mm |
| 1 | 11.5 | 2.49 | 2.18 | 90 | 2.09 | 1.81 | 110 | 1.51 |
| 2 | 11.5 | 2.83 | 2.52 | 100 | 2.31 | 2.03 | 120 | 1.81 |
| 3 | 12.0 | 2.44 | 2.13 | 90 | 2.08 | 1.83 | 108 | 1.49 |
| 4 | 3.0 | 1.40 | 1.30 | 30 | 1.29 | 1.20 | 31 | 1.19 |
| 5 | 40.0 | 3.53 | 3.40 | 140 | 3.39 | 3.30 | 180 | 3.29 |

It should be noted that a wall thickness of the artery sheath 1 is less than or equal to 0.40 mm, and a wall thickness of the guiding catheter 2 is less than or equal to 0.30 mm; the difference of an outer diameter of the guiding catheter 2 and an inner diameter of the artery sheath 1 is greater than or equal to 0.003 mm, so a certain gap is reserved for allowing the guiding catheter 2 to penetrate into the artery sheath 1; and the difference of an outer diameter of the myocardial biopsy forceps 3 and an inner diameter of the guiding catheter 2 is greater than or equal to 0.003 mm, so a certain space in the guiding catheter 2 is guaranteed for an operation.

Before an operation, forms of the guiding catheter 2, the angiography catheter 4 and the Pigtail catheter may be forms as shown in FIG. 2 or FIG. 4 or other forms of catheters applied in the art.

A cardiac or vascular interventional operation may be performed via a radial artery or ulnar artery, which may be specifically determined according to blood vessel conditions of a patient.

It should be noted that expect for the aforementioned specific embodiments, the device for performing cardiology and endovascular interventional operations via a radial artery or ulnar artery in this embodiment may further be applied to other cardiac and vascular interventional operations, which may be performed by those skilled in the art with an understanding of the concept of the present invention, so no more examples are described hereinafter.

Finally, it can be understood that the above embodiments are only exemplary embodiments for describing the principle of the present invention, but not to limit the present invention. Those of ordinary skills in the art may make various modifications and variations without departing from the principle and essence of the present invention, and such modifications and variations are within the protection scope of the present invention.

The invention claimed is:

1. A method for performing cardiology and endovascular interventional operations via a radial artery or ulnar artery, comprising:
   step 1, putting an artery sheath into a punctured artery through a puncture site, wherein the artery is the radial artery or ulnar artery, and wherein the artery sheath is connected to a hemostasis valve;
   penetrating a Pigtail catheter into a first end of the artery sheath from outside the body and penetrating it out of the artery sheath from a second end of the artery sheath, and advancing it to a left ventricle;
   injecting contrast into the Pigtail catheter to perform left ventricle angiography; and
   withdrawing the Pigtail catheter from the artery sheath after completing the left ventricle angiography;
   step 2, penetrating a guiding catheter into the first end of the artery sheath from outside the body and penetrating it out of the artery sheath from the second end, and advancing it to the left ventricle;
   step 3, advancing a myocardial biopsy forcep to a left ventricle endocardium through the guiding catheter to collect a piece of myocardium;
   step 4, withdrawing the myocardial biopsy forcep from the guiding catheter to be outside the body, and preserving a myocardium specimen;
   step 5, repeating the step 3 and the step 4 until collecting enough number of myocardium specimens; and
   step 6, withdrawing the guiding catheter from the artery sheath, pulling the artery sheath out of the artery, and performing compression dressing over the puncture site.

2. The method of claim 1, before the step 2, further comprising the following steps:
   penetrating an angiography catheter into the first end of the artery sheath from outside the body and penetrating it out of the artery sheath from the second end, and advancing it to an aortic sinus;
   injecting contrast into the angiography catheter to perform coronary angiography; and
   withdrawing the angiography catheter from the artery sheath after completing the coronary angiography.

3. The method of claim 1, before the step 1, further comprising the step of: performing sterilization, draping and local anesthesia on the puncture site of the radial artery or ulnar artery.

4. The method of claim 1, before the step 6, further comprising the step of: injecting contrast into the guiding catheter to perform left ventricle angiography.

5. A method of applying an artery sheath for performing cardiology and endovascular interventional operations, comprising:
   step 1, penetrating a guiding catheter into a first end of an artery sheath from outside the body and penetrating it out of the artery sheath from a second end, and advanced advancing it to an aortic sinus, wherein the artery sheath was previously inserted into a punctured artery through a puncture site, and wherein the punctured artery is the radial artery or ulnar artery, and wherein the artery sheath is connected to a hemostasis valve;
   step 2, injecting contrast through the guiding catheter to perform coronary angiography, and/or inserting one or more coronary interventional devices to through the guiding catheter to perform one or more coronary interventional operations;
   step 3, advancing the guiding catheter to a left ventricle after completing the coronary angiography and/or the one or more coronary interventional operations;
   step 4, advancing a myocardial biopsy forcep to a left ventricle endocardium through the guiding catheter to collect a piece of myocardium;

step 5, withdrawing the myocardial biopsy forcep from the guiding catheter to be outside the body, and preserving a myocardium specimen;

step 6, repeating the step 4 and the step 5 until collecting enough number of myocardium specimens; and step 7, withdrawing the guiding catheter from the artery sheath, pulling the artery sheath out of the artery, and performing compression dressing over the puncture site.

6. The method of claim 5, before the step 7, further comprising the step of: injecting contrast into the guiding catheter to perform left ventricle angiography.

7. A method of applying an artery sheath for performing cardiology and endovascular interventional operations, wherein the artery sheath is placed in a punctured radial artery or ulnar artery via a puncture site, comprising:

step 1, penetrating a guiding catheter into a first end of the artery sheath from outside the body and penetrating it out of the artery sheath from a second end of the artery sheath, and advancing it to a peripheral artery, and wherein the artery sheath is connected to a hemostasis valve;

step 2, injecting contrast through the guiding catheter to perform peripheral artery angiography, and/or inserting peripheral artery interventional devices through the guiding catheter to the peripheral artery to perform one or more peripheral artery interventional therapy operations;

step 3, advancing the guiding catheter to a left ventricle after completing the peripheral artery angiography and/or the one or more peripheral artery interventional therapy operations;

step 4, advancing a myocardial biopsy forcep to a left ventricle endocardium through the guiding catheter to collect a piece of myocardium;

step 5, withdrawing the myocardial biopsy forcep from the guiding catheter to be outside the body, and preserving a myocardium specimen; and step 6, withdrawing the guiding catheter from the artery sheath, pulling the artery sheath out of the radial artery or ulnar artery, and performing compression dressing over the puncture site.

8. The method of claim 7, before the step 6, further comprising the step of: injecting contrast into the guiding catheter to perform left ventricle angiography.

9. A system for performing cardiology and endovascular interventional operations via a radial artery or ulnar artery, comprising an artery sheath, a guiding catheter and a myocardial biopsy forcep, wherein the artery sheath is connected to a hemostasis valve and is configured to be placed into a punctured radial artery or ulnar artery, the guiding catheter is configured to be inserted through the artery sheath into the radial artery or ulnar artery and to be advanced to an aorta, a peripheral artery, an aortic sinus or a left ventricle, and wherein the myocardial biopsy forcep is configured to be inserted into the guiding catheter and advanced to the left ventricle and is configured to collect a piece of myocardium; and wherein the system further comprises a Y-shaped hemostasis valve, wherein the Y-shaped hemostasis valve comprises a first port, a second port and a third port, wherein the first port of the Y-shaped hemostasis valve is configured to linearly communicate with the second port of the Y-shaped hemostasis valve, wherein a hemostasis valve body is disposed within the second port of the Y-shaped hemostasis valve, wherein the first port of the Y-shaped hemostasis valve is configured to communicate with an in-vitro port of the guiding catheter, and wherein the myocardial biopsy forcep is configured to be inserted into the second port of the Y-shaped hemostasis valve and advanced via the guiding catheter.

10. The system of claim 9, further comprising a three-way stopcock, a pressure transducer, a pressure monitor and a contrast injection subsystem for injecting contrast into the system, wherein a first port of the three-way stopcock is configured to communicate with the third port of the Y-shaped hemostasis valve, wherein the third port of the Y-shaped hemostasis valve is configured to be in communication with the first port of the Y-shaped hemostasis valve, a second port of the three-way stopcock is configured to be connected to the pressure transducer and the contrast injection subsystem, and the pressure transducer is configured to be connected to the pressure monitor.

11. The system of claim 10, wherein a rotary switch is disposed at the three-way stopcock and is configured to connect or disconnect any two ports of the three-way stopcock.

12. The system of claim 9, further comprising an angiography catheter, wherein the angiography catheter is configured to penetrate out of the artery sheath into the artery and to be advanced to an aorta, a peripheral artery, an aortic sinus or a left ventricle.

13. The system of claim 12, further comprising a three-way stopcock, a pressure transducer, a pressure monitor and a contrast injection subsystem for injecting contrast into the system, wherein a first port of the three-way stopcock is configured to communicate with an in-vitro port of the angiography catheter, a second port of the three-way stopcock is configured to be connected to the pressure transducer and the contrast injection subsystem, and the pressure transducer is configured to be connected to the pressure monitor.

14. The system of claim 9, further comprising a Pigtail catheter, wherein the Pigtail catheter is configured to penetrate out of the artery sheath into the artery and to be advanced to an aorta, a peripheral artery, an aortic sinus or a left ventricle.

15. The system of claim 14, further comprising a three-way stopcock, a pressure transducer, a pressure monitor and contrast injection subsystem for injecting contrast into the system, wherein a first port of the three-way stopcock is configured to communicate with an in-vitro port of the Pigtail catheter, a second port of the three-way stopcock is configured to be connected to the pressure transducer and the contrast injection subsystem, and the pressure transducer is configured to be connected to the pressure monitor.

16. The system of claim 9, wherein the size ranges of a length, an outer diameter and an inner diameter of the artery sheath are 3-40 cm, 1.40-3.53 mm and 1.30-3.40 mm, respectively, the size ranges of a length, an outer diameter and an inner diameter of the guiding catheter are 30-140 cm, 1.30-3.40 mm and 1.20-3.30 mm, respectively, and the size ranges of a length and an outer diameter of the myocardial biopsy forceps are 31-180 cm and 0.10-3.30 mm, respectively.

17. The system of claim 9, wherein the difference of an outer diameter of the guiding catheter and an inner diameter of the artery sheath is greater than or equal to 0.003 mm, and the difference of an outer diameter of the myocardial biopsy forceps and an inner diameter of the guiding catheter is greater than or equal to 0.003 mm.

\* \* \* \* \*